United States Patent
Pang

(10) Patent No.: US 6,319,691 B1
(45) Date of Patent: Nov. 20, 2001

(54) FUSION PROTEINS COMPRISING IFN-ALPHA2B AND TM-ALPHA1

(75) Inventor: Danny Zhong Der Pang, Fullerton, CA (US)

(73) Assignee: USA Universe Bioengineering, Inc., Anaheim, CA (US)

( * ) Notice: Subject to any disclaimer, the term of this patent is extended or adjusted under 35 U.S.C. 154(b) by 0 days.

(21) Appl. No.: 09/333,348

(22) Filed: Jun. 15, 1999

(51) Int. Cl.[7] .............................. C12P 21/04; C12N 15/00; C12N 5/00; A61K 38/21; C07K 17/00
(52) U.S. Cl. .................. 435/69.7; 435/69.51; 435/320.1; 435/325; 424/85.7; 530/351
(58) Field of Search .................. 530/351; 435/69.51, 435/69.7, 325, 320.1; 424/85.7

(56) References Cited

U.S. PATENT DOCUMENTS 5,114,711 * 5/1992 Bell et al. ........................ 424/85.1
5,916,773 * 6/1999 Mele et al. ....................... 435/69.7

OTHER PUBLICATIONS

Jeong, J.–Y., et al. (Jul. 1996) J. Biochem. Mol. Biol. 29(4): 365–71.*

* cited by examiner

*Primary Examiner*—Yvonne Eyler
*Assistant Examiner*—Janet L. Andres

(57) ABSTRACT

A fusion protein which comprises human IFN-alpha2b and human TM-alpha1. Such fusion proteins have enhanced biological activity and are useful for the treatment of viral, neoplastic and immunodeficiency diseases.

4 Claims, No Drawings

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1
agccatgggc tgtgatctgc ctcaa                                              25

<210> SEQ ID NO 2
<211> LENGTH: 30
<212> TYPE: DNA
<213> ORGANISM: Artificial Sequence
<220> FEATURE:
<223> OTHER INFORMATION: Synthetic Primer

<400> SEQUENCE: 2
taagcttttt cattccttac ttcttaaact                                         30

<210> SEQ ID NO 3
<211> LENGTH: 17
<212> TYPE: DNA

```
<213> ORGANISM: Artificial Sequence
<220> FEATURE:
<223> OTHER INFORMATION: Synthetic Primer

<400> SEQUENCE: 3
attaaccctc actaaag                                                      17

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
taatacgact cactataggg                                                   20

<210> SEQ ID NO 5
<211> LENGTH: 28
<212> TYPE: DNA
<213> ORGANISM: Artificial Sequence
<220> FEATURE:
<223> OTHER INFORMATION: Synthetic Primer

<400> SEQUENCE: 5
agccatggca tcagacgcag ccgtagac                                          28

<210> SEQ ID NO 6
<211> LENGTH: 31
<212> TYPE: DNA
<213> ORGANISM: Artificial Sequence
<220> FEATURE:
<223> OTHER INFORMATION: Synthetic Primer

<400> SEQUENCE: 6
ccaagcttta ctagtcatcc tcgtcggtct t                                      31

<210> SEQ ID NO 7
<211> LENGTH: 36
<212> TYPE: DNA
<213> ORGANISM: Artificial Sequence
<220> FEATURE:
<223> OTHER INFORMATION: Synthetic Primer

<400> SEQUENCE: 7
agagccaccg ccacccgatt ccttacttct taaact                                 36

<210> SEQ ID NO 8
<211> LENGTH: 36
<212> TYPE: DNA
<213> ORGANISM: Artificial Sequence
<220> FEATURE:
<223> OTHER INFORMATION: Synthetic Primer

<400> SEQUENCE: 8
tcgggtggcg gtggctctga cgcagccgta gacacc                                 36

<210> SEQ ID NO 9
<211> LENGTH: 30
<212> TYPE: DNA
<213> ORGANISM: Artificial Sequence
<220> FEATURE:
<223> OTHER INFORMATION: Synthetic Primer

<400> SEQUENCE: 9
taagctttac taattttctg cctcttccac                                        30
```

```
<210> SEQ ID NO 10
<211> LENGTH: 597
<212> TYPE: DNA
<213> ORGANISM: Human
<220> FEATURE:
<221> NAME/KEY: CDS
<222> LOCATION: 1...597

<400> SEQUENCE: 10 tgt gat ctg cct caa acc cac agc ctg ggt agc agg agg acc ttg atg      48
Cys Asp Leu Pro Gln Thr His Ser Leu Gly Ser Arg Arg Thr Leu Met
 1               5                  10                  15 ctc ctg gca cag atg agg aga atc tct ctt ttc tcc tgc ttg aag gac      96
Leu Leu Ala Gln Met Arg Arg Ile Ser Leu Phe Ser Cys Leu Lys Asp
             20                  25                  30 aga cat gac ttt gga ttt ccc cag gag gag ttt ggc aac cag ttc caa     144
Arg His Asp Phe Gly Phe Pro Gln Glu Glu Phe Gly Asn Gln Phe Gln
         35                  40                  45 aag gct gaa acc atc cct gtc ctc cat gag atg atc cag cag atc ttc     192
Lys Ala Glu Thr Ile Pro Val Leu His Glu Met Ile Gln Gln Ile Phe
 50                  55                  60 aat ctc ttc agc aca aag gac tca tct gct gct tgg gat gag acc ctc     240
Asn Leu Phe Ser Thr Lys Asp Ser Ser Ala Ala Trp Asp Glu Thr Leu
 65                  70                  75                  80 cta gac aaa ttc tac act gaa ctc tac cag cag ctg aat gac ctg gaa     288
Leu Asp Lys Phe Tyr Thr Glu Leu Tyr Gln Gln Leu Asn Asp Leu Glu
                 85                  90                  95 gcc tgt gtg ata cag ggg gtg ggg gtg aca gag act ccc ctg atg aag     336
Ala Cys Val Ile Gln Gly Val Gly Val Thr Glu Thr Pro Leu Met Lys
            100                 105                 110 gag gac tcc att ctg gct gtg agg aaa tac ttc caa aga atc act ctc     384
Glu Asp Ser Ile Leu Ala Val Arg Lys Tyr Phe Gln Arg Ile Thr Leu
            115                 120                 125 tat ctg aaa gag aag aaa tac agc cct tgt gcc tgg gag gtt gtc aga     432
Tyr Leu Lys Glu Lys Lys Tyr Ser Pro Cys Ala Trp Glu Val Val Arg
        130                 135                 140 gca gaa atc atg aga tct ttt tct ttg tca aca aac ttg caa gaa agt     480
Ala Glu Ile Met Arg Ser Phe Ser Leu Ser Thr Asn Leu Gln Glu Ser
145                 150                 155                 160 tta aga agt aag gaa tcg ggt ggc ggt ggc tct gac gca gcc gta gac     528
Leu Arg Ser Lys Glu Ser Gly Gly Gly Gly Ser Asp Ala Ala Val Asp
                165                 170                 175 acc agc tcc gaa atc acc acc aag gac tta aag gag aag aag gaa gtt     576
Thr Ser Ser Glu Ile Thr Thr Lys Asp Leu Lys Glu Lys Lys Glu Val
            180                 185                 190 gtg gaa gag gca gaa aat tag                                         597
Val Glu Glu Ala Glu Asn
        195

<210> SEQ ID NO 11
<211> LENGTH: 198
<212> TYPE: PRT
<213> ORGANISM: Human

<400> SEQUENCE: 11

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
             20                  25                  30
```

-continued

```
Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                   80

Leu Asp Lys Phe Tyr Thr Glu Leu Tyr Gln Gln Leu Asn Asp Leu Glu
            85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Ser Gly Gly Gly Ser Asp Ala Ala Val Asp
            165                 170                 175

Thr Ser Ser Glu Ile Thr Thr Lys Asp Leu Lys Glu Lys Lys Glu Val
            180                 185                 190

Val Glu Glu Ala Glu Asn
            195
```

FUSION PROTEINS COMPRISING IFN-ALPHA2B AND TM-ALPHA1

BACKGROUND OF THE INVENTION

This invention relates to the field of DNA recombinant technology. More specifically, this invention relates to fusion proteins comprising human IFN-alpha2b and human TM alpha1 and pharmaceutical compositions containing the fusion proteins and methods for using them.

Interferons (IFN) are a family of polypeptides synthesized and secreted by a large variety of eukaryotic cells in response to viral infections or to various synthetic and biological inducers, including viral constituents, double stranded RNA, and mitogens. Human IFNs are classified into two major groups. The IFNs-alpha, -beta, and -omega are designated type I IFNs, and IFN-gamma is designated type II IFN. All type I IFNs exhibit high homology in their primary, secondary, and tertiary structures. They interact with the same receptor and activate similar transcriptional signaling pathways, eliciting a similar range of biological responses, including antiviral, antiproliferative, and immunomodulatory activities. Binding to a quite distinct cell surface receptor than type I IFN, Type II IFN differs from type I IFN in many aspects, such as the structure and induction of the gene, IFN's antigenicity, and biological responses. Type II IFN has a different range of immune functions such as macrophage activation.

In the human IFN system, there is only one IFN-beta, one IFN-omega, and one IFN-gamma gene, and there are at least 14 nonallelic IFN-alpha genes, which are located on chromosome 9 (Allen and Fantes, *Nature* 287:408, 1980; Owerback et al., *Proc. Natl. Acad. Sci.* 78:3123, 1981; Henco et al., *J. Mol. Biol.* 185:227, 1985; Diaz et al., *J. Interferon Res.* 11, S85, 1991; Diaz et al., *J. Interferon Res.* 13:61, 1993). Among the IFN-alpha genes, IFN-alpha2 (also called IFN-alpha A) gene locus is also found to contain three allelic variants, IFN-alpha2a, IFN-alpha2b, and IFN-alpha2c (Goeddel et al., *Nature* 287:411, 1980; Streuli et al., *Science* 209:1343, 1980; Lee et al., *J. Interferon Res.* 15:341, 1995). These three variants are unique among IFN-alpha genes in coding for mature proteins of 165 amino acids, since all other IFN-alpha proteins have 166 amino acids. Analysis of the cloned DNA sequences of these three IFN-alpha2 variants indicated they differ from each other in nucleotides(nt) at one or two positions (nt 137 and 170) in the coding region of the gene, resulting in a substitution of a lysine for arginine at position 23 in the mature IFN-alpha2a protein and an arginine for histidine at position 34 in the mature IFN-alpha2c proteins. Differing in only a few nucleotides, the purified IFN-alpha2a, 2b, and 2c are shown to differ significantly in their biologic and antigenic properties, indicating that differences in the amino acid sequences at position 23 and 34 may be significant in changing the immunogenicity as well as the structure and function of IFN-alpha2 (Von Gabain et al., *Eur. J Biochem.* 190:257, 1990). Naturally, IFN-alpha2b is predominant in the IFN-alpha2 species, as the IFN-alpha2 is predominant in the IFN-alpha species produced by normal human leukocytes (Emanuel and Pestka, *J. Biol. Chem.* 268: 12565, 1993; Gewert et al., *J. Interferon Res.* 13: 227, 1993; Dopaola et al., *J. Interferon Res.* 14:325, 1994). Among more than 24 IFN-alpha species identified so far from gene and protein sequence data, the predominant subspecies, IFN-alpha 2, is the most intensively studied (Weissmann and Weber, *Prog Nucleic Acid Res. Mol. Biol.* 33:251, 1986; Zoon, K. C., *Interferon* 9:1, 1987; Pestka et al., *Ann. Rev. Biochem.* 56:727, 1987).

Human IFN-alpha2 was among the first of the IFNs to be cloned by recombinant DNA technology. The recombinant version of IFN-alpha2, such as IFN-alpha2a, alpha2b or alpha2c, consists of a single unglycosylated species of IFN protein with a molecular weight of 19 Kd and a pI in the range of 5.5–6.5. Two IFN-alpha2 recombinant products, IFN-alpha2a (ROFERON, Hoffman-La Roche) and IFN-alpha2b (INTRON, Schering Plough), are commercially available. They are approved worldwide for the treatment of a variety of diseases including various cancers, particularly hematological malignancies such as hairy cell leukemia and chronic myelogenous leukemia, and viral induced disorders, such as hepatitis (Main et al., *Antivir. Chem. Chemother.* 9:449, 1998; Oren et al., *Ann. Hematol.* 77:187, 1998; Bruno et al., *Ann. Intern. Med.* 128:956, 1998; Hassanein et al., *J. Viral. Hepat.* 3:333, 1996; Dorr, R. T., *Drugs* 45:177, 1993).

Many IFN-alpha hybrids, conjugates and chimeras are disclosed in attempt to create IFN-alpha molecules with advantageous properties (U.S. Pat. Nos. 4,678,751; 5,071,761; 5,738,846; 5,594,107; Sperber et al., *Antiviral. Res.* 22:121, 1993; Rasch et al., *Dig. Dis. Sci.* 43:1719, 1998; He et al., *J. Cancer Res. Clin. Oncol.* 125:77, 1999).

A standard cell-free protein extract preparation from the thymus gland, known as thymosin fraction V (TF5) (U.S. Pat. No. 4,082,737), was demonstrated to be a potent immunopotentiating preparation. TF 5 can suppress to various extents immune deficiency diseases and can also act in lieu of the thymus gland to reconstitute immune functions in thymic deprived and/or immunodeprived individuals (Wara et al., *N. Engl. J. Med* 292: 70, 1975). Analytical polyacrylamide gel electrophoresis and isoelectric focusing have demonstrated that TF5 consists of a number of polypeptides termed thymosin, with molecular weights ranging from 1,000 to 15,000.

The first of these peptides to be purified to homogeneity and sequenced from TF5 was called thymosin alpha 1 (TM-alpha1) (Goldstein et al., *Proc. Natl. Acad. Sci.* 74:725, 1977; U.S. Pat. No. 4,079,127). The chemical synthesis of TM-alpha1 by solution and solid phase synthesis techniques is described in U.S. Pat. Nos. 4,148,788 and 5,856,440. Identical to the native TM-alpha1 in the biological potent and amino acid sequence with lack of the N-terminal acetyl group, recombinant TM-alpha1 can be produced in *E. coli* by recombinant DNA cloning techniques (Wetzel et al., *Biochemistry* 19:6096, 1980). TM-alpha1 analogs and derivatives also have been produced, U.S. Pat. Nos. 4,116,951 and 5,512,656. TM-alpha1 is a 28 amino acid acidic peptide with a molecular weight of 3,100 and a pI in the range of 4.0–4.3. TM-alpha1 maintains many of the biologic effects of TF5 and has been found to be 10 to 1,000 times more active than TF5 in a number of bioassay systems designed to measure the maturation and function of T lymphocytes.

TM-alpha1 potentiates the immune system by stimulating alpha- and gamma-interferon production, increasing T cell numbers, increasing production of macrophage migration inhibitory factor, inducing expression of T-cell markers, including interleukin-2 receptors, and improving T-cell helper cell activity (Marshall et al., *J. Immunol.* 126:741, 1981; Mutchnick et al., *Clin. Immunol. Immunopathol.* 23:626, 1982; Low et al., *Thymus* 6:27,1984; Sztein et al., *Proc. Natl. Acad. Sci.* 83:6107, 1986; Serrate et al., *J. Immunol.* 1939:2338,1987; Baxevanis et al., *Immunopharm.* 13:133, 1987; and, Svedersky, L. P., *Eur. J. Immunol.*

12:244, 1982). TM-alpha1 is currently under clinical trial to determine its efficacy in the treatment of immunodeficiency diseases, immunodepressed cancer patients and chronic active hepatitis (Goldstein, A. L., *Cancer Invest.* 12:545, 1994; Lopez et al., *Ann. Oncol.* 5:741, 1994; Garaci et al., *Eur. J. Cancer.* 31A:2403,1995; Garaci et al., *Mech. Ageing. Dev.* 96:103, 1997; Bonkovsky, H. L., *Hepatology* 26(3 Suppl 1):143S, 1997; Liaw, Y. F., *J. Gastroenterol. Hepatol.* 12:S346, 1997).

Clinical studies have demonstrated that the combination therapy of IFN-alpha2 and TM-alpha1 is more effective than either IFN-alpha2 and TM-alpha1 alone in treatment of cancers and chronic hepatitis (Garaci et al., *Int. J. Clin. Lab. Res.* 24:23, 1994; Garaci et al., *J. Immunother.* 13:7, 1993; Garaci et al., *Eur. J. Cancer* 31A:2403, 1995; U.S. Pat. No. 5,849,696; Rasi et al., *Gut* 39:679, 1996; Sherman et al., *Hepatology* 27:1128, 1998; Moscarella et al., *Liver* 18:366, 1998).

Although the exact mechanism of action of IFN-alpha2 and TM-alpha1 in the treatment of the above mentioned diseases is not fully understood, their biological activities are mediated by binding to specific cell surface receptors. IFN-alpha2 and TM-alpha1 each bind to their respective receptors, resulting in a biological signal transduction to various effector cells. Studies of the receptor binding for IFN-alpha2 and TM-alpha1 indicate that IFN-alpha2 and TM-alpha1 share a sequence homology and compete with each other for high-affinity receptors on murine thymocytes. These studies showed that binding of $.^{125}$I-labelled octapeptide (fragment 130–137 of IFN-alpha2) to high-affinity receptors on thymocytes is efficiently inhibited by both unlabelled IFN-alpha2 and unlabelled TM-alpha1 (Zav'yalov et la., *FEBS Lett.* 278:187, 1991). Further studies also showed that prothymosin alpha (proTM-alpha) competes with $.^{125}$I-labelled IFN-alpha2 for binding the same receptor on human fibroblasts (Zav'yalov et la., *Mol. Biol.* 32: 425, 1995). ProTM-alpha, a 113 amino acid thymic polypeptide, was named because it was thought to be a precursor to TM-alpha1. ProTM-alpha includes thymosin-alpha1 as its 28 N-terminal amino acids and possess the same approximate quantitative and qualitative biological activity that has been ascribed to TM-alpha1 (U.S. Pat. No. 4,716,148; Smith, M. R., *Leukemia and Lymphoma* 18:209, 1995). This direct competition between IFN-alpha2 and TM-alpha1/proTM-alpha for a single cell surface receptor indicates that a single receptor is capable of binding both IFN-alpha2 and TM-alpha1/proTM-alpha. However, it is not yet clear whether the heterogeneity in IFN-alpha2 and TM-alpha1/proTM-alpha binding is due to the existence of a shared receptor subunit within the multisubunit complexes of the IFN-alpha2 and TM-alpha1/proTM-alpha receptors, or due to the existence of a coreceptor which is distinct from that which binds IFN-alpha2 alone or TM-alpha1/proTM-alpha alone, or due to the distinct binding manner in ligand-receptor interactions that results in different tertiary structures within the intracellular portion of the receptor chains leading to a specific signaling (Lewerenz et al., *J. Mol. Biol.* 282:585, 1998; Russell-Harde et al., *Biochem. Biophy. Res. Communic.* 255:539, 1999). Therefore, the receptor, which binds to the IFN-alpha2/TM-alpha1 fusion proteins, will be referred to herein as the IFN-alpha2/TM-alpha1 receptor.

BRIEF SUMMARY OF THE INVENTION

The present invention relates to fusion proteins comprising IFN-alpha2b and TM-alpha1. The fusion proteins of this invention are represented by the following formulas:

I-T, T-I, I-L-T, or T-L-I where I is IFN-alpha2b; T is TM-alpha1; and L is a peptide linker. IFN-alpha2b is fused to TM-alpha1 either directly or through a peptide linker. In preferred aspects, IFN-alpha2b and TM-alpha1 are linked together via a linker to produce a single protein which retains the biological activity of IFN-alpha2b and TM-alpha1. This invention also relates to pharmaceutical compositions containing the fusion molecules.

The fusion proteins of the present invention may be characterized by possessing both biological properties of IFN-alpha2b and TM-alpha1 or they may be further characterized by possessing advantageous antiviral, antiproliferative and immunomodulatory properties above their parental peptides combined. Such fusion proteins have the characteristics of being unique to viral, neoplastic and immunodeficiency diseases and are useful for therapeutic purposes.

DETAILED DESCRIPTION OF THE INVENTION

The present invention is directed to fusion proteins comprising IFN-alpha2 and TM-alpha1.

1. Definition

In describing the present invention, the following terms are intended to be defined as indicated below.

"Recombinant" polypeptides refer to polypeptides produced by recombinant DNA techniques; i.e., produced from cells (microbial or mammalian transformed by an exogenous DNA construct encoding the desired polypeptide. Polypeptides expressed in most bacterial cultures, e.g., *E. coli*, will be free of glycan. Polypeptide expressed in yeast may have a glycosylation pattern different from that expressed in mammalian cells.

"Native" proteins or polypeptides refer to proteins or polypeptides recovered from a source occurring in nature. Thus, the term "native TM alpha1" would include naturally occurring TM alpha1 and fragments thereof.

A DNA "coding sequence" is a DNA sequence which is transcribed into mRNA and translated into a polypeptide in a host cell when placed under the control of appropriate regulatory sequences. The boundaries of the coding sequence are determined by a start codon at the 5' N-terminus and a translation stop codon at the 3' C-terminus. A coding sequence can include prokaryotic sequences, cDNA from eukaryotic mRNA, genomic DNA sequences from eukaryotic DNA, and even synthetic DNA sequences. A transcription termination sequence will usually be located 3' to the coding sequence.

"Fusion protein" is a protein resulting from the expression of at least two operatively-linked heterologous coding sequences. The protein comprising IFN-alpha2b peptide and TM-alpha1 peptide sequences of this invention is an example of a fusion protein.

"Nucleotide sequence" is a heteropolymer of deoxyribonucleotides (bases adenine, guanine, thymine, or cytosine). DNA sequences encoding the fusion proteins of this invention can be assembled from synthetic or cDNA-derived DNA fragments and short oligonucleotide linkers to provide a synthetic gene which is capable of being expressed in a recombinant expression vector. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

"Recombinant expression vector" is a replicable DNA construct used either to amplify or to express DNA encoding the fusion proteins of the present invention. A expression vector contains DNA control sequences and a coding sequence. DNA control sequences include promoter sequences, ribosome binding sites, polyadenylation signals, transcription termination sequences, upstream regulatory domains and enhancers. Recombinant expression systems as defined herein will express the fusion proteins upon induction of the regulatory elements.

"Transformed host cells" refer to cells that have been transformed and transfected with exogenous DNA. Exogenous DNA may or may not be integrated (covalently linked) to chromosomal DNA making up the genome of the cell. In prokaryotes and yeast, for example, the exogenous DNA may be maintained on an episomal element, such as a plasmid or stably integrated into chromosomal DNA. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

"PCR" means polymerase chain reaction which is based on a thermostable DNA polymerase from Thermus aquaticus. The PCR technique refers to a DNA amplification skill that mimics the natural DNA replication process in that the DNA molecules doubles after each thermal cycle, in a way similar to in vivo replication. The DNA polymerase mediates extension in a 5' to 3' direction. The "primer" refers to an oligonucleotide sequence that provides an 3' end to which the DNA polymerase adds nucleotides complementary to a nucleotide sequence. The "template" refers to a nucleotide sequence to which the primers are annealed.

2. Interferon Alpha 2

The term interferon alpha 2 (IFN-alpha2) refers to proteins having amino acid sequences which are substantially similar to the native human IFN-alpha2 amino acid sequences and which are biologically active in that they are capable of binding to IFN-alpha2 receptors, transducing a biological signal initiated by binding IFN-alpha2 receptors, or cross-reacting with anti-IFN-alpha2 antibodies raised against IFN-alpha2. IFN-alpha2 has three variants (IFN-alpha2a, -alpha2b, and -alpha2c) which differ from each other in nucleotides (nt) at one or two positions (nt 137 and 170) in the coding region of the gene, resulting in changes of one or two amino acids. IFN-alpha2a (Lys$^{23}$His$^{34}$) is distinguishable from IFN-alpha2b (Arg$^{23}$His$^{34}$) and IFN-alpha2c (Arg$^{23}$Arg$^{34}$) by the presence of lysine instead of arginine at amino acid position 23. IFN-alpha2c (Arg$^{23}$Arg$^{34}$) differs from IFN-alpha2a (Lys$^{23}$His$^{34}$) and IFN-alpha2b (Arg$^{23}$His$^{34}$) by the presence of an arginine instead of histidine at amino acid position 34 (Goeddel et al., Nature 287:411, 1980; Streuli et al., Science 209:1343, 1980; Lee et al., J. Interferon Res. 15:341, 1995). IFN-alpha2b was selected as the fusion partner for the IFN-alpha2b/TM-alpha1 fusion proteins of the invention, although the IFN-alpha2a or any other IFN species can be used as well. IFN-alpha2 polypeptides and DNA sequences encoding IFN alpha2 are disclosed, for example, in Goeddel et al., Nature 287:411, 1980; Goeddel et al., Nature 290:20, 1981; Streuli et al., Science 209:1343, 1980, and Gewert et. al., J. Interferon Res. 13:227, 1993.

As used herein, The term "IFN-alpha2" also includes analogs of IFN-alpha2 molecules which exhibit at least some biological activity in common with native human IFN-alpha2. Exemplary analogs of IFN-alpha2 are disclosed in U.S. Pat. Nos 5,609,868; 5,071,761; 5,541,293 and Davis et al., Int. J. Pept. Protein Res. 29:685, 1987. Other IFN-alpha2 analogs which are described herein may also be used to construct fusion proteins with TM-alpha1. Furthermore, those skilled in the art of mutagenesis will appreciate that other analogs, as yet undisclosed or undiscovered, may be used to construct IFN-alpha2b/TM-alpha1 fusion proteins as described herein.

3. Thymosin Alpha1

The term thymosin alpha 1 (TM-alpha1) refers to proteins having amino acid sequences which are substantially similar to the native human TM-alpha1 amino acid sequences and which are biologically active in that they are capable of binding to thymosin receptors, transducing a biological signal initiated by binding TM-alpha1 receptors, or cross-reacting with anti-TM-alpha1 antibodies raised against TM-alpha1. Such sequences are disclosed, for example, in U.S. Pat. No. 4,079,127.

The term "TM-alpha1" also includes analogs of TM-alpha1 molecules which exhibit at least some biological activity in common with native human TM-alpha1. Exemplary analogs of TM-alpha1 are disclosed in U.S. Pat. Nos. 4,116,951; 4,466,918; and 5,512,656. Other TM-alpha1 analogs which are described herein may also be used to construct fusion proteins with thymosin. Furthermore, those skilled in the art of mutagenesis will appreciate that other analogs, as yet undisclosed or undiscovered, may be used to construct IFN-alpha2b/TM-alpha1 fusion proteins as described herein.

4. Fusion Proteins Comprising IFN-alpha2b and TM-alpha1

The term "fusion protein" herein refers to the protein resulting from the expression of IFN-alpha2b and TM-alpha1 operatively-linked heterologous coding sequences. The fusion proteins of the present invention include constructs in which the C-terminal portion of IFN-alpha2b is fused to the N-terminal portion of TM-alpha1, and also constructs in which the C-terminal portion of TM-alpha1 is fused to the N-terminal portion of IFN-alpha2b. IFN-alpha2b is fused to TM-alpha1 either directly or through a linker. Specifically, the fusion proteins of the present invention are represented by the following formulas:

I-T, T-I, I-L-T, or T-L-I where I is IFN-alpha2b; T is TM-alpha1; and L is a peptide linker. Specific fusion protein constructs are named by listing the IFN-alpha2b and TM-alpha1 domains in the fusion protein in their order of occurrence (with the N-terminal domain specified first, followed by the C-terminal domain). Thus, IFN-alpha2b/TM-alpha1 refers to a fusion protein comprising IFN-alpha2b followed by TM-alpha1 (i.e., the C-terminus of IFN-alpha2b is fused to the N-terminus of TM-alpha1).

Unless otherwise specified, the terms IFN-alpha2b/TM-alpha1 and TM-alpha1/IFN-alpha2b refer to fusion proteins with a peptide linker added. IFN-alpha2b is fused to TM-alpha1 in such a manner as to produce a single protein which retains the biological activity of IFN-alpha2b and TM-alpha1.

Examples of fusion proteins comprising IFN-alpha2b and TM-alpha1 are shown in the accompanying Sequence Listing. SEQ ID NO:10 shows the nucleotide sequence and corresponding amino acid sequence of a human IFN-alpha2b/TM-alpha1 fusion protein. The fusion protein comprises human IFN-alpha2b (amino acids 1–165) linked to human TM-alpha1 (amino acids 172–199) via a linker sequence (amino acids 166–171), as shown in SEQ ID NO:11.

Equivalent fusion proteins may vary from the sequence of SEQ ID NO: 10 and SEQ ID NO: 11 by one or more substitutions, deletions, or additions, the net effect of which is to retain biological activity of the protein when derived as a fusion protein comprising IFN-alpha2 and TM-alpha1.

5. Construction of cDNA Sequences Encoding Fusion Proteins Comprising IFN-alpha2b and TM-alpha1

A DNA sequence encoding a fusion protein is constructed using recombinant DNA techniques to assemble separate DNA fragments encoding IFN-alpha2b and TM-alpha1 into an appropriate expression vector. For example, the 3' end of a DNA fragment encoding IFN-alpha2b is ligated to the 5' end of the DNA fragment encoding TM-alpha1, with the reading frames of the sequences in phase to permit mRNA translation of the sequences into a single biologically active fusion protein. The resulting protein is fusion protein comprising IFN-alpha2b and TM-alpha1. Alternatively, the 3' end of a DNA fragment encoding TM-alpha1 may be ligated to the 5' end of the DNA fragment encoding IFN-alpha2b, with the reading frames of the sequences in phase to permit mRNA translation of the sequences into a single biologically active fusion protein. The regulatory elements responsible for transcription of DNA into mRNA are retained on the first of the two DNA sequences, while stop codons, which would prevent read-through to the second DNA sequence, are eliminated. Conversely, regulatory elements are removed from the second DNA sequence while stop codons required to end translation are retained.

The IFN-alpha2b is fused to TM-alpha1 with or without a linker. In preferred aspects of the present invention, the IFN-alpha2b and TM-alpha1 domains are linked through a peptide linker consisting of 5 to about 15 genetically encodable amino acids.

The linker sequence is incorporated into the fusion protein construct by well-known standard PCR extension methods as described below.

6. Proteins and Analogs

The present invention provides a fusion protein comprising human IFN-alpha2b and human TM-alpha1. Derivatives and analogs of the fusion proteins of the present invention may also be obtained by modifying the primary amino acid structure with other chemical moieties, by mutations of the fusion protein, by linking particular functional groups to amino acid side chains or at the N- or C-termini, or by conjugating the fusion protein with other proteins or polypeptides. Bioequivalent analogs of the fusion proteins may also be constructed by making various substitutions of residues or sequences.

7. Expression of Recombinant Fusion Proteins Comprising IFN Alpha2b and TM Alpha1

There are several ways to express the recombinant fusion proteins in vitro, including in *E. coli,* baculovirus, yeast, mama cells or other expression systems.

The prokaryotic system, *E. coli,* is not able to do post-translational modification, such as glycosylation. But this is probably not a problem for the IFN-alpha2b/TM-alpha1 fusion proteins since the native IFN-alpha2b and TM-alpha1 are not heavily glycosylated. Further, it has been reported that recombinant IFN-alpha2b and TM-alpha1 without any glycosylation retained their biological activities (Baron and Narula, Bio/technology 10:179, 1990; Wetzel et al., *Biochemistry* 19:6096, 1980). With the prokaryotic system, the expressed protein is either present in the cell cytoplasm in an insoluble form so-called inclusion bodies or is found in the soluble fraction after the cell has been lysed (Thatcher & Panayotatos, *Methods Enzymol.* 119:166, 1986; Goeddel et al., *Nature* 287:411,1980; Dworkin-Rastl et al., *Gene* 21:237, 1983). If the expressed protein is in insoluble inclusion bodies, solubilization and subsequent refolding of the inclusion bodies is usually required (Schein and Noteborn, *Bio/technology* 6:291, 1988; Wilkinson and Harrison, *Bio/technology* 9:443, 1991).

Many prokaryotic expression vectors are known to those of skill in the art, such as pKK223-3 (Pharmacia Fine Chemicals, Uppsala, Sweden), pKK233-2 (Clontech, Palo Alto, Calif., USA), and pGEM1 (Promega Biotech, Madison, Wis., USA), which are commercial available. Another exemplary prokaryotic expression vector is pZD20, described in Example 1 below.

Promoters commonly used in recombinant microbial expression systems include the beta-lactamase (penicillinase) and lactose promoter system (Chang et al., *Nature* 275:6, 1978; Goeddel et al., *Nature* 281:544, 1979), the tryptophan (trp) promoter system (Goeddel et al., *Nucl. Acids Res.* 8:4057, 1980) and tac promoter (Maniatis, *Molecular Cloning: A Laboratory Mannual,* Cold Spring Harbor Laboratory, page 412, 1982). A particularly useful bacterial expression system employs the phage lamda $P_L$ promoter and cIts857 thermoinducible repressor (Bernard et al., *Gene* 5:59, 1979; Love et al., *Gene* 176:49, 1996).

Recombinant fusion proteins may also be expressed in yeast hosts such as *Saccharomyces cerevisiae* and *Pichia pastoris.* It usually gives the ability to do various post-translational modifications. The expressed fusion protein can be secreted into the culture supernatant where not many other proteins reside, making protein purification easier. Yeast vectors for expression of the fusion proteins in this invention contain certain requisite features. The elements of the vector are generally derived from yeast and bacteria to permit propagation of the plasmid in both. The bacterial elements include an origin of replication and selectable marker. The yeast elements include an origin of replication sequence (ARS), a selectable marker, a promoter, and a transcriptional terminator.

Suitable promoters in yeast vectors for expression include the promoters of the TRP1 gene, the ADHI or ADHII gene, acid phosphatase (PH03 or PH05) gene, isocytochrome gene, or the promoters involved with the glycolytic pathway, such as the promoter of enolase, glyceraldehyde-3-phosphate dehydrogenase (GAPDH), 3-phosphoglycerate kinase (PGK), hexokinase, pyruvate kinase, triosephosphate isomerase and phosphoglucose isomerase (Hitzeman et al., *J. Biol. Chem.* 255:2073, 1980; Hess et al., *J. Adv. Enzyme Reg.* 7:149, 1968; and Holland et al., *Biochem.* 17:4900, 1978).

Commercial available yeast vectors include pYES2, pPIC9 (Invitrogen, San Diego, Calif.), YEpc-pADH2a, pYcDE-1 (Washington Research, Seattle, Wash.), pBC102-K22 (ATCC# 67255), and YpGX265GAL4 (ATCC# 67233).

Mammalian cell lines, such as the COS-7, L cells, C127, 3T3, Chinese hamster ovary (CHO), Hela and BHK, can be employed to express the recombinant fusion proteins in this invention. The recombinant proteins produced in mammalian cells are normally soluble and glycosylated and have an authentic N-terminal. Mammal expression vectors may contain non-transcribed elements such as an origin of replication, promoter and enhancer, and 5' or 3' nontranslated sequences such as ribosome binding sites (RBS), a polyadenylation site, acceptor sites and splice donor, and transcriptional termination sequences. Promoters for use in mammalian expression vectors usually are for example viral promoters, such as Polyoma, Adenovirus, HTLV, Simian Virus 40 (SV40), and human cytomegalovirus (CMV). An example of the mammalian expression vectors is pcDNA3, ((Invitrogen, San Diego, Calif.), which contains a CMV promoter and a NEO resistance gene.

Depending on the expression system and host selected, a homogeneous recombinant fusion protein can be obtained by some of the purification steps, in various combinations, of the conventional chromatographys of protein purification, which include immunoaffinity chromatography, reverse phase chromatography, cation exchange chromatography, anion exchange chromatography, hydrophobic interaction chromatography, gel filtration chromatography and high performace liquid chromatography (HPLC). If the expression system secretes the fusion protein into growth media, the protein can be purified directly from the media. If the fusion protein is not secreted, it is isolated from cell lysates. Cell disruption can be done by any conventional method, including freeze-thaw cycling, sonication, mechanical disruption, or use of cell lysing agents.

Fusion protein compositions can be prepared for administration by combining fusion protein having the desired degree of purity and the pharmaceutically effective amount with physiologically acceptable carriers.

Fusion protein compositions may be used to enhance proliferation, maturation and functional activation of T cells, or to enhance antiviral, antiproliferative and immunomodulatory effects. Specifically, compositions containing the fusion protein may be used to enhance the immune system to battle against viral, neoplastic and immunodeficiency diseases. To achieve this result, a pharmaceutically effective quantity of a fusion protein composition is administered to a mammal, preferably a human, in association with a pharmaceutically acceptable carrier.

The following examples are offered to further illustrate the invention and are not intended to be limitative thereof:

EXAMPLE 1

Synthesis of Expression Vectors Encoding an IFN Alpha2b/TM Alpha1 Fusion Protein
1. Cell Culture and RNA Extraction Peripheral blood monocytes (PBMs) were isolated from buffy coats by Ficoll-Hypaque density centrifugation. PBMs were repeatedly washed with steril PBS (phosphate-buffered saline) and spinned down by centrifugation. The cells at 5 times.10.sup.6 cells/ml were cultured for 18 hours in 175 cm sup.2. flaskes at 37.degree. C. and 5% CO.sub.2 in air in 100 ml RPMI supplemented with 10% fetal calf serum, 1% phytohemagglutinin (PHA) and 100 units huIL-2/ml. Phorbol 12-myristate 13-acetate (PMA) was then added to the culture at a final concentration of 50 .mu.g/ml. The culture was continued for another 6 hours at 37.degree. C. and 5% CO.sub.2in air before the cells were havested by centrifugation. RNA was extracted by the guanidinium CsCl method and poly A$^+$ RNA was prepared by oligo-dT cellulose chromatography (Maniatis et al., *Molecular Cloning: A Laboratory Manual,* Cold Spring Harbor, 1982).

The first-strand cDNA was synthesized from poly A+ RNA by reverse transcription (RT) using AMV reverse transcriptase with oligo(dT) as a 3' primer in 10 mM Tris-HCl (pH 9.0), 50 mM KCl, 1.5 mM MgCl.sub.2 and 0.5 mM dNTPs in a total of 50 mu.l volume. The reaction mixture was incubated at a 42.degree. C. water bath for 60 minutes, followed by a dilution with 50 .mu.l of DEPC treated water. After being boiled for 3 minutes and cooled on ice for 2 minutes, the reaction mixture was used directly as the templates for PCR to amplify IFN-alpha2b cDNA and TM-alpha1 cDNA.

2. Amplification and Cloning of cDNAs Encoding Human IFN-alpha2

The cDNA of IFN-alpha2b was rendered double-stranded using Taq DNA polymerase and a set of upstream and downstream oligonucleotide primers for human IFN-alpha2b. The primers used to amplify the IFN-alpha2b are shown in Table 1. The 5' primer (IFN-A) contained a NcoI site and the coding sequence for the first 5 amino acids from the IFN-alpha2b. The 3' primer (IFN-B) contained a HindIII site and coding sequence for the last 6 amino acids from the IFN-alpha2b. The PCR buffer contained 50 mM KCl, 10 mMTris-HCl (pH9.0), 1.5 mM MgCl.sub.2, 0.01% gelatin, 0.05 mmol each of DNTP, 1.0 .mu.mol of each primers, 10.mu.l reverse transcription reaction mixture, and 2 units of Taq DNA polymerase in a total of 50 .mu.l volume. The PCR condition was 94.degree. C. for 30 seconds, 55.degree. C. for 30 seconds, and 72.degree. C. for 30 seconds for 25 cycles in the MJ Research model PTC-1 152 thermocycler (Watertown, Mass.).

TABLE 1

| Primers used in PCR to amplify human IFN-alpha2b | | |
|---|---|---|
| Designation Primer Sequence | | Primer Length |
| IFN-A | 5' AGCCATGGGCTGTGATCTGCCTCAA 3' (SEQ ID NO:1) | 25 |
| IFN-B | 5' TAAGCTTTTTCATTCCTTACTTCTTAAACT 3' (SEQ ID NO:2) | 30 |

The PCR amplified DNA fragments were directly cloned into pBT/T vectors and then transformed into competent E.coli DH5.alpha. cells. pBT/T vector is derived from pBluescript II KS(+) cloning vector (Stratagene, La Jolla, Calif.) by creating 3'-T overhangs at its MCS (multiple cloning sites). The PCR cDNA fragments with 3'-A overhangs can be ligated into pBT/T cloning vectors without any digestion of restriction endonuclease. Designing the restriction endonuclease sites NcoI and HindIII in the primers is for subcloning the cDNA fragments into expression vectors at the sites NcoI/HindIII.

The competent cells of DH5.alpha were prepared by the CaCl.sub.2 method (Mandel and Higa, *J. Mol. Biol.* 53:159, 1970). Briefly, 50 ml of LB medium without antibiotics is inoculated with a single *E. coli* DH5.alpha colony and grown overnight at 37.degree. C. with shaking at 250 rpm. The overnight culture is diluted 1:50 with LB medium mined by digestion with restriction endonucleases NcoI and HindIII. The DNA from one of the clones (plasmid pB/IFN-alpha2b) was sequenced in both directions with the primers shown in Table 2 by the chain termination method (Sanger et al., *Pro. Natl. Acad. Sci.* 74:5463, 1977).

TABLE 2

Primers used for sequencing

| Designation | Primer Sequence | | Primer Length |
|---|---|---|---|
| T3 | 5' ATTAACCCTCACTAAAG | (SEQ ID NO:3) | 17 |
| T7 | 5' TAATACGACTCACTATAGGG | (SEQ ID NO:4) | 20 | without any antibiotic and continued the cultivation at 37.degree. C. with 250 rpm until an OD.sub.590 reaches 0.3–0.5. The culture is then placed on ice for 10 minutes and centrifuged 10 minutes at 3000 rpm at 4.degree. C. The supernatant is discarded. The cell pellet is resuspended gently in 40% of the starting volume with the ice-cold 0.1 M CaCl.sub.2 solution. The cell suspension is kept on ice for 30 minutes and then spinned down at 3000 rpm for 10 minutes at 4.degree. C. The pellet is resuspended again in 2% of the starting volume with the ice-cold 0.1 M CaCl.sub.2 solution, transferred into a sterile polypropylene tube, and then chilled on ice overnight at 4.degree. C. Cold sterile 80%

3. Amplification and Cloning of cDNAs Encoding Human proTM-alpha

The cDNA of the human proTM-alpha was also obtained by reverse transcription and PCR performed the same way as described above. The primers for the PCR are shown in Table 3. The 5' primer (TM-A) contained a NcoI site and the coding sequence for the first 6 amino acids from TM-alpha1. The 3' primer (proTM-B) contained a HindIII site and coding sequence for the last 6 amino acids from the proTM-alpha.

TABLE 3

Primers used in PCR to amplify human pro TM-alpha

| Designation | Primer Sequence | | Primer Length |
|---|---|---|---|
| TM-A | 5' AGCCATGGCATCAGACGCAGCCGTAGAC 3' | (SEQ ID NO:5) | 28 |
| proTM-B | 5' CCAAGCTTTACTAGTCATCCTCGTCGGTCTT 3' | (SEQ ID NO:6) | 31 | glycerol in distilled water is added into the cell suspension to a final concentration of 20% and mixed gently. The competent cells, at a density of approximately 1 times10.sup.9/ml are stored in a 40 microliter aliquot at −70.degree. C.

For transformation, an aliquot of the competent *E. coli* strain DH5.alpha. cells are thawed on ice and transferred into an eppendorf tube containing approximately 10 ng plasmid DNA. The mixture is left on ice for 30 minutes and mixed by swirling gently. The cells are heatshocked at 42.degree. C. for exactly 45 seconds in a circulating water bath that has been preheated at 42.degree. C. The cells are rapidly returned to an ice bath and allowed to chill for 2 minutes. Ten volumes of SOC medium are added to the tube. The cells are incubated at 37.degree. C. for 60 minutes with shaking at 250 rpm to allow the bacteria to recover and to express the antibiotic resistant marker encoded by the plasmid. Transformed competent cells are transferred onto 90-mm agar plates containing the antibiotic and gently spread over the surface of the agar plate using a sterile bent glass rod. The plates are left at room temperature until the liquid has been absorbed. The plates are from the media. If the fusion protein is not secreted, it is isolated from cell lysates. Cell then inverted and incubated at 37.degree C. overnight.

Plasmid DNA was obtained from small overnight cultures by a modified alkaine lysis method (Lee and Rashid, *Bio-Techniques* 9:676, 1990). The size of the inserts was deter The PCR amplified DNA fragments were directly cloned into pBT/T vectors and then transformed into competent *E.coli* DH5.alpha. Isolation of plasmid DNA and determination of the size of the insert were performed as described above. The DNA from one of the clones (plasmid pB/proTM-alpha) was sequenced in both directions with the primers shown in Table 2 by the chain termination method.

4. Synthesis and Cloning of IFN-alpha2/TM-alpha1 Fusion cDNA (a). Synthesis of cDNA Encoding IFN Alpha2b and a Linker pB/IFN-alpha2b was prepared by the digestion with restriction endonuclease BamHI and used as a template for PCR to generate and amplify the cDNA containing the IFN-alpha2b and a linker. The linker is attached to the 3' end of IFN-alpha2b and the fragment is named IFN-alpha2b-L. PCR performed the same way as described above. The primers for PCR amplification are shown in Table 4. 5' primer (IFN-A) contained a NcoI site and the coding sequence for the first 5 amino acids from the IFN-alpha2b. The 3' primer (IFN-L-B) contained the sequence coding for the linker and the last 6 amino acids from the IFN-alpha2b.

TABLE 4

Primers used in PCR to generate and amplify IFN-alpha2b-L

| Designation | Primer Sequence | | Primer Length |
|---|---|---|---|
| IFN-A | 5' AGCCATGGGCTGTGATCTGCCTCAA 3'    IFN-alpha2b | (SEQ ID NO:1) | 25 |
| IFN-L-B | 5' AGAGCCACCGCCACCCGATTCCTTACTTCTTAAACT 3'   Linker — (3' end)IFN-alpha2b | (SEQ ID NO:7) | 36 |

The amplified PCR products were gel-purified and stored at −20.degree. C. until used for preparation of IFN alpha2b/ TM alpha1 cDNA.

(b). Synthesis of cDNA Encoding TM-alpha1 and a Linker pB/proTM-alpha was prepared by digestion with restriction enzyme BamHI and used as a template for PCR to generate and amplify the cDNA containing TM-alpha1 and a linker. The linker is attached to the 5' end of TM-alpha1 and the fragment is named L-TM-alpha1. PCR performed the same way as described above. The primers for PCR amplification are shown in Table 5. 5' primer (L-TM-A) contained the sequence coding for the linker and the first 7 amino acids from the TM-alpha1. The 3' primer (TM-B) contained a HindIII site and the coding sequence for the last 6 amino acids from the TM-alpha1.

(c). Synthesis of cDNA Encoding IFN Alpha2b/TM Alpha1 and its Expression Construct IFN-alpha2/TM-alpha1 fusion cDNA was generated by PCR using the mixture (1:1 ratio) of IFN-alpha2b-L and L-TM-alpha1 as templates. PCR performed the same way as described above. The primers for PCR amplification are shown in Table 6. 5' primer (IFN-A) contained a NcoI site and the coding sequence for the first 5 amino acids from the IFN-alpha2b. The 3' primer (TM-B) contained a HindIII site and the coding sequence for the last 6 amino acids from the TM-alpha1.

TABLE 5

Primers used in PCR to generate and amplify L-TM-alpha1

| Designation | Primer Sequence | | Primer Length |
|---|---|---|---|
| L-TM-A | 5' TCGGGTGGCGGTGGCTCTGACGCAGCCGTAGACACC 3'   Linker — (5' end)TM-alpha1 | (SEQ ID NO:8) | 36 |
| TM-B | 5' TAAGCTTTACTAATTTTCTGCCTCTTCCAC 3'   TM-alpha1 | (SEQ ID NO:9) | 30 |

The amplified PCR products were gel-purified and stored at −20.degree. C. until used for preparation of IFN alpha2b/ TM alpha1 cDNA.

TABLE 6

Primers used in PCR to generate and amplify fusion cDNA, IFN-alpha2b/TM-alpha1

| Designation | Primer Sequence | | Primer Length |
|---|---|---|---|
| IFN-A | 5' AGCCATGGGCTGTGATCTGCCTCAA 3'   IFN-alpha2b /NcoI | (SEQ ID NO:1) | 25 |
| TM-B | 5' TAAGCTTTACTAATTTTCTGCCTCTTCCAC 3'   TM-alpha1 /HindIII | (SEQ ID NO:9) | 30 |

Products of the PCR amplification were cloned into pBT/T vectors and then transformed into competent *E. coli* strain DH5.alpha. cells. Isolation of the plasmid DNA and determination of the size of the insert were performed as described above. The DNA from one of the clones (plasmid pB/IFN-alpha2b/TM-alpha1) was sequenced in both directions with the primers shown in Table 2 by the chain termination method. The DNA sequencing confirms that the insert of the plasmid pB/IFN-alpha2b/M-alpha1 contains the IFN-alpha2b and TM-alpha1 linked together via the linker with the correct reading frames in phase. The sequence of the insert determined is designated IFN-alpha2b/TM-alpha1 and is shown in SEQ ID NO:10.

EXAMPLE 2
Expression and Purification of IFN-alpha2b/TM-alpha1 Fusion Protein For expression of the IFN-alpha2b/TM-alpha1 fusion gene, the plasmid pB/IFN-alpha2b/TM-alpha1 was digested with restriction endonucleases NcoI and HindIII to release the insert containing the IFN-alpha2b/TM-alpha1. The DNA fragments were then gel purified and then ligated to the prokaryotic expression vectors pZD20 through the NcoI and HindIII sites. After ligation, the DNA was transformed into competent *E. coli* MM294 cells. The plasmids isolated from one of the colonies were designated as expression plasmid pIFN-alpha2b/TM-alpha1 and digested with restriction endonucleases NcoI and HindIII to confirm the size of the insert. The pZD20 expression vector is derived from pCE30 vector (ATCC# 37830), which contains a tandem-arranged bacteriophage lambda promoters, P.sub.R and P.sub.L, and the lambda cI857 gene (Elvin, et al., *Gene* 87:123, 1990).

Plasmid pIFN-alpha2b/TM-alpha1 is deposited with the American Type Culture Collection (ATCC) as a patent deposit at 10801 University Blvd., Manassas, Va. 20110: Accession number: PTA-41; Deposit date May 11, 1999: and designated as plasmid pIFN-alpba2b/TM-alpha1 (*E. coli* MM 294/pIFN-alpha2b/TM-alpha1 as the host vector system).

The *E. coli* MM294 cells containing the expression vector p/IFN-alpha2b/TM-alpha1 were grown overnight in LB broth containing 100 .mu.g/ml ampicillin at 30.degree. C., with rotary shaking at 225 rpm. The overnight culture was diluted 1:10 with M9 minimal medium supplemented with 2.0% casamino acids. The MM294 cells were grown at 30.degree. C. until the OD.sub.680 of the culture reached 3.0 at which time the temperature was raised to 42.degree. C. The cultivation was continued for another 6 hours in that matter. The cells were harvested by centrifugation and the bacterial pellets were stored at −80.degree. C. until further purification.

For purification of IFN-alpha2b/TM-alpha1 fusion proteins, the frozen *E. coli* cell pellets were suspended in 6 volumes of lysis buffer (50 mM Tris HCl, pH 8.0, 1 mM EDTA, 1 mM DTT, 1 mM phenylmethanesulfonyl fluoride, 2 mg/ml lysozyme) and disrupted by sonication (25 ml aliquots with a 5mm probe, 50 W, on ice for 10 minutes). The insoluble inclusion bodies isolated from the cell lysate by centrifugation were solubilized in 8 M urea in 100 mM Tris-acetate/NaOH, pH 9.5, 25 mM EDTA, 5 mM DTT. Extracted fusion proteins were subjected to refolding reaction at a redox buffer (50 mM Tris HCl, pH 9.0, 5 mM EDTA, 0.2 mM oxidized glutathione and 0.4 mM reduced glutathione). The renatured fusion protein solution was further purified to homogeneity in a series of column chromatographic purifications.

Briefly, the renatured fusion protein solution was loaded onto an immunoaffinity column equilibrated with Tris buffer (25 mM Tris HCl, pH 8.0, 200 mM NaCl). The affinity column was washed with the equilibrated buffer until the absorbance of the eluate was zero or nearly zero, and then eluted with acetate buffer (100 mM acetic acid, pH 2.0, 150 mM NaCl). The fusion protein pool was then adjusted to pH 4.5 with 1.0 N NaOH and diluted with 5-fold cold water to its conductivity about 9 mS/cm (microsiemens/cm). After being adjusted to 20 mM sodium acetate, pH 4.5, the sample was loaded onto a SP-Sepharose Fast Flow column equilibrated with 20 mM sodium acetate, pH 4.0. After the column was washed with five column volumes of 20 mM sodium acetate, pH 4.5, the fusion protein was eluted with 400 mM sodium acetate, pH 4.5. The material eluted from the cation exchange column was diluted to an OD.sub.280 of 1.0 with 10 mM sodium phosphate, pH 7.0 and adjusted to a final ammonium sulphate concentration of 1.2 M by the addition of solid (NH.sub.4).sub.2 SO.sub.4. The sample was filtered with a 0.45 micron filter to remove the precipitation and loaded onto a Phenyl Sepharose High Performance column which had been equilibrated with 1.2 M ammonium sulphate, 10 mM sodium phosphate, pH 7.0. The fusion protein was eluted with a linear gradient from 100% loading conditions to 100% 10 mM sodium phosphate, 30% (v/v) ethylene glycol, pH 7.0. The eluate of the hydrophobic interaction chromatography was concentrated with an Amicon concentrator Stirred cell 2000 and then applied to a gel filtration column (Sephacryl S-200 HR) equilibrated with 20 mM phosphate-citrate buffer, pH 7.2. The fusion protein peak was then recovered. All the purification steps were carried out at 4.degree. C.

The IFN-alpha2b/TM-alpha1 fusion protein exmples were analyzed under standard reducing conditions in 15% SDS polyacrylamide gel electrophoresis (SDS-PAGE) (Laemmli, *Nature* 277:680,1970). The protein bands are visualized by Coomassie blue staining. The apparent molecular weight of the fusion protein is about 23 kd. When examined by Western blot (Towbin et al., *Proc. Natl. Acad. Sci.* 76:4350, 1979; Burnette, *Anal. Biochem.* 112:195, 1981), it was found that the IFN-alpha2b/TM-alpha1 contains the human IFN-alpha2 component. The concentration of the fusion proteins was determined with the BioRad Protein Assay. This assay uses the dye Coomassie brilliant blue and measures the protein/dye complex at 595 nm. The standard used is bovine serum albumin.

EXAMPLE 3
Antiviral Properties of IFN-alpha2b/TM-alpha1 Fusion Proteins

One of the biological assays for the fusion protein comprising IIN-alpha2b and TM-alpha1 was an antiviral assay. Antiviral specific activity of the fusion protein was determined on both human and bovine cells by using cytopathic effect (CPE) inhibition assays as reviewed previously (Stewart, The Interferon System, Springer-Verlag, 17–18, 1979). Briefly, 100 .mu.l of WISH (human amniotic cell line, ATCC) and MDBK (bovine kidney cell line, ATCC) cells suspension (4 times10.sup.5 cells/ml) were seeded in 96-well microplates, respectively. 100 .mu.l of two-fold serial diluted interferon preparations was added to each well. After incubation for 24 hours at 37.degree. C. and 5% CO.sub.2 in air, the cells were infected with vesicular stomatitis virus (VSV) ( Indiana strain, ATCC), followed by an additional 24 hours incubation. Every sample was done in triplicate. The CPE was checked under a microscopy on virus control, cell control and cells which received NIH standard interferon. The highest dilution giving 50% reduction of the viral plaques was considered as the end point. The interferon unit was defined as the reciprocal of the dilution at the 50% end point and was adjusted to the NIH interferon reference standard (Ga23-902-530). The results are reported in Table 7 below.

TABLE 7

Antiviral activity of fusion proteins using VSV as the challenge virus

| | Specific activity/mg protein | |
|---|---|---|
| Interferon | WISH | MDBK |
| IFN-alpha2b | $1.91 \times 10^8$ lu | $2.58 \times 10^8$ lu |
| IFN-alpha2b/TM-alpha1 | $1.69 \times 10^8$ lu | $2.28 \times 10^8$ lu |

The specific biological activity of the IFN-alpha2b or the IFN-alpha2b/TM-alpha1 is presented as the number of biological units per mg of the total protein present. The data in Table 7 show that the specific CPE activities on human WISH and bovine MDBK cells are similar between IFN-alpha2b and IFN-alpha2b/TM-alpha1, although the MDBK cell line is more sensitive than the WISH.

EXAMPLE 4
Immunological Activity of IFN-alpha2b/TM-alpha1 in E-rosette Assay The E-rosette bioassay performed in this invention is based on the observations that the addition of optimally active thymosin preparation can increase in patients with thymus hypoplasia the percent and absolute number of peripheral blood T cells forming rosette with sheep red blood cells (Wara et al., *N. Engl. J Med.* 292:70, 1975), and that thymic extracts can restore the erythrocyte rosette-forming capacity of alpha-amanitin-treated lymphocytes (Sattar et al., *Immunol. Lett.* 27:221, 1991). In fact, the percentage of E-rosette forming cells in peripheral human blood can be a measure of the content of fully mature T-cells. In a healthy adult the normal level of E-rosettes is about 56%.

For the performance of the E-rosette assay, a RNA polymerase inhibitor, alpha-amanitin, was used. In brief, human peripheral blood lymphocytes were separated by Ficoll-Hypaque gradient centrifugation, washed and resuspended in RPMI medium. After being blocked with alpha-amanitin, the cells were incubated with varying concentrations of either synthetic TM-alpha1 or the IFN-alpha2b/TM-alpha1 fusion protein, followed by the addition of sheep red blood cells. A rosette was defined as a lymphocyte that bound three or more sheep erythrocytes. Rosettes enumerated under a microscope by counting 200 lymphocytes. The results were expressed as per cent lymphocytes forming rosettes. The value of the normal level of E-rosette in the healthy adult is taken as 100% in a relative numerical scale, and after the alpha-amanitin blockage it is taken as 0%. Each data point was done in duplicate. The results are shown in Table 8.

TABLE 8

E-rosette assay in comparison of the fusion protein with synthetic TM-alpha1

| Synthetic TM-alpha1 (.mu.g/0.5 ml culture) | E-rosette number (%) | IFN-alpha2b/TM-alpha1 (.mu.g/0.5 ml culture) | E-rosette number (%) |
|---|---|---|---|
| 6.0 | 30 | 5.0 | 29 |
| 3.0 | 52 | 2.5 | 50 |
| 1.5 | 62 | 1.25 | 72 |
| 0.75 | 100 | 0.63 | 100 |
| 0.38 | 57 | 0.31 | 56 |
| 0.19 | 34 | 0.156 | 31 |

In a comparison of synthetic TM-alpha1 with the fusion protein, it appears that the IFN-alpha2b/TM-alpha1 fusion protein shows a stronger immunological action than synthetic TM-alpha1. It has been demonstrated that the IFN-alpha2b/TM-alpha1 fusion proteins possess the TM-alpha1's action on the differentiating mechanism and on the maturation of thymus-related lymphocytes to immune-competent T cells.

I claim:

1. A recombinant expression plasmid comprising DNA coding for a fusion protein comprising IFN-alpha2b and TM-alpha1 wherein the plasmid is designated as p/IFN-alpha2b/TM-alpha1 and deposited with the American Type Culture Collection under accession number PTA-41.

2. A fusion protein comprising IFN-alpha2b and TM-alpha1 encoded by the plasmid of claim 1.

3. A host cell comprising the plasmid according to claim 1, wherein said host cell is selected from a group consisting of mammalian, plant, insect, yeast, and bacterial cells.

4. A process of production of a fusion protein comprising IFN-alpha2/TM-alpha1, comprising cultivating the host cell of claim 3 and isolating the expressed fusion protein.

* * * * *